US008876718B2

(12) United States Patent
Osawa

(10) Patent No.: US 8,876,718 B2
(45) Date of Patent: Nov. 4, 2014

(54) ULTRASOUND DIAGNOSTIC APPARATUS AND ULTRASOUND IMAGE GENERATING METHOD

(75) Inventor: Atsushi Osawa, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 0 days.

(21) Appl. No.: 13/593,033

(22) Filed: Aug. 23, 2012

(65) Prior Publication Data

US 2013/0079638 A1 Mar. 28, 2013

(30) Foreign Application Priority Data

Sep. 27, 2011 (JP) .................. 2011-210349

(51) Int. Cl.
*A61B 8/08* (2006.01)
*H01L 41/187* (2006.01)
*H01L 41/193* (2006.01)
*H01L 41/08* (2006.01)
*A61B 8/00* (2006.01)

(52) U.S. Cl.
CPC .......... *H01L 41/1875* (2013.01); *H01L 41/193* (2013.01); *H01L 41/0825* (2013.01); *A61B 8/4483* (2013.01); *A61B 8/4494* (2013.01)
USPC ............................. 600/443; 600/437; 600/439

(58) Field of Classification Search
CPC .......... A61B 8/08; A61B 8/44; A61B 8/4444; A61B 8/4483; A61B 8/4494
See application file for complete search history.

(56) References Cited

U.S. PATENT DOCUMENTS

| | | | |
|---|---|---|---|
| 2005/0107700 A1* | 5/2005 | Morris et al. | 600/437 |
| 2009/0048522 A1* | 2/2009 | Huang | 600/459 |
| 2011/0062824 A1* | 3/2011 | Wada | 310/334 |
| 2011/0077520 A1* | 3/2011 | Osawa | 600/443 |
| 2011/0125024 A1* | 5/2011 | Mueller et al. | 600/459 |

FOREIGN PATENT DOCUMENTS

| | | |
|---|---|---|
| JP | 6-30934 A | 2/1994 |
| JP | 09033638 A | 2/1997 |
| JP | 11-155863 A | 6/1999 |
| JP | 2011-010794 | 1/2011 |
| JP | 2011-62224 A | 3/2011 |
| JP | 2011-160856 A | 8/2011 |
| WO | WO 2010/131394 A1 | 11/2010 |

OTHER PUBLICATIONS

Japanese Office Action dated Sep. 17, 2013, issued in corresponding Japanese Patent Application No. 2011-210349 (partial translation is provided).
Japanese Office Action dated Mar. 11, 2014, issued in corresponding Japanese patent Application No. 2011-210349 (partial translation is provided).

* cited by examiner

*Primary Examiner* — Tse Chen
*Assistant Examiner* — Mark Remaly
(74) *Attorney, Agent, or Firm* — Birch, Stewart, Kolasch & Birch, LLP

(57) ABSTRACT

An ultrasound diagnostic apparatus includes an ultrasound transducer unit having inorganic piezoelectric elements arranged in layer form and organic piezoelectric elements arranged in layer form, the inorganic piezoelectric elements and the organic piezoelectric elements being stacked on each other with a first acoustic matching layer provided therebetween, a transmission circuit for transmitting ultrasound from the inorganic piezoelectric elements through the organic piezoelectric elements serving as a second acoustic matching layer, a reception circuit for using the organic piezoelectric elements as non-resonant reception devices to receive an ultrasonic echo and thereby obtain reception signals and processing the reception signals so as to generate sample data, and an image generating unit for generating an ultrasound image based on the sample data generated by the reception circuit.

9 Claims, 2 Drawing Sheets

ULTRASOUND DIAGNOSTIC APPARATUS AND ULTRASOUND IMAGE GENERATING METHOD

BACKGROUND OF THE INVENTION

The present invention relates to an ultrasound diagnostic apparatus and an ultrasound image generating method, and particularly to an ultrasound diagnostic apparatus adapted to perform ultrasound transmission and reception using an arrayed organic piezoelectric elements.

In the medical field, ultrasound diagnostic apparatus employing ultrasound images have already been put to practical use. A typical ultrasound diagnostic apparatus for medical use transmits an ultrasonic beam from ultrasound transducers toward the inside of a subject, receives an ultrasonic echo from the subject on the ultrasound transducers, and electrically processes a reception signal corresponding to the received echo so as to generate an ultrasound image.

Recently, an increasing attention is captured by the harmonic imaging technology in which a harmonic component caused by the distortion in ultrasound waveform due to the non-linearity of a subject is received for imaging in order to conduct a more accurate diagnosis.

Such an ultrasound transducer unit as disclosed in JP 11-155863 A, for instance, is proposed as suitable for harmonic imaging, in which a plurality of inorganic piezoelectric elements having inorganic piezoelectric bodies of lead zirconate titanate (PZT) or the like and a plurality of organic piezoelectric elements having organic piezoelectric bodies of polyvinylidene fluoride (PVDF) or the like are stacked on each other.

An ultrasonic beam can be transmitted by the inorganic piezoelectric elements with high output and harmonic signals can be received by the organic piezoelectric elements with high sensitivity.

Between the inorganic piezoelectric elements and the organic piezoelectric elements, an acoustic matching layer is provided in order to efficiently deliver the ultrasound as emitted from the inorganic piezoelectric elements. The acoustic matching layer has a thickness meeting λ/4 resonance conditions with respect to the wavelength λ of a fundamental wave transmitted from the inorganic piezoelectric elements, which prevents reflection from the surface of the acoustic matching layer. In addition, the acoustic matching layer is formed of a material having an acoustic impedance of a medium value between the acoustic impedance values of the inorganic piezoelectric elements and of a subject as the living body, so as to carry out matching of acoustic impedances, that is to say, so as to cause ultrasound transmitted from the inorganic piezoelectric elements to efficiently enter the inside of the subject.

The inorganic piezoelectric elements and the subject, however, are quite different from each other in intrinsic acoustic impedance and, consequently, one acoustic matching layer may not be enough for an adequate matching effect.

It is possible indeed to use a plurality of acoustic matching layers with different acoustic impedances as stacked on one another in the order of acoustic impedance value, but the structure of an ultrasound transducer unit will be complicated.

SUMMARY OF THE INVENTION

The present invention was made in order to solve the above problems with the prior art, aiming at providing an ultrasound diagnostic apparatus and an ultrasound image generating method allowing an efficient delivery of ultrasound and generation of an ultrasound image of high quality with an ultrasound transducer unit having a simple structure.

An ultrasound diagnostic apparatus according to the present invention comprises: an ultrasound transducer unit having inorganic piezoelectric elements arranged in layer form and organic piezoelectric elements arranged in layer form, the inorganic piezoelectric elements and the organic piezoelectric elements being stacked on each other with a first acoustic matching layer provided therebetween; a transmission circuit for transmitting ultrasound from the inorganic piezoelectric elements through the organic piezoelectric elements serving as a second acoustic matching layer; a reception circuit for using the organic piezoelectric elements as non-resonant reception devices to receive an ultrasonic echo and thereby obtain reception signals, and processing the reception signals so as to generate sample data; and an image generating unit for generating an ultrasound image based on the sample data generated by the reception circuit.

An ultrasound image generating method according to the present invention comprises the steps of: using an ultrasound transducer unit having inorganic piezoelectric elements arranged in layer form and organic piezoelectric elements arranged in layer form, the inorganic piezoelectric elements and the organic piezoelectric elements being stacked on each other with a first acoustic matching layer provided therebetween, to transmit ultrasound from the inorganic piezoelectric elements through the organic piezoelectric elements serving as a second acoustic matching layer; using the organic piezoelectric elements as non-resonant reception devices to receive an ultrasonic echo; and generating an ultrasound image based on reception signals obtained by the organic piezoelectric elements.

DETAILED DESCRIPTION OF THE INVENTION

In the following, an embodiment of the present invention is described in reference to the accompanying drawings.

Figure 1:
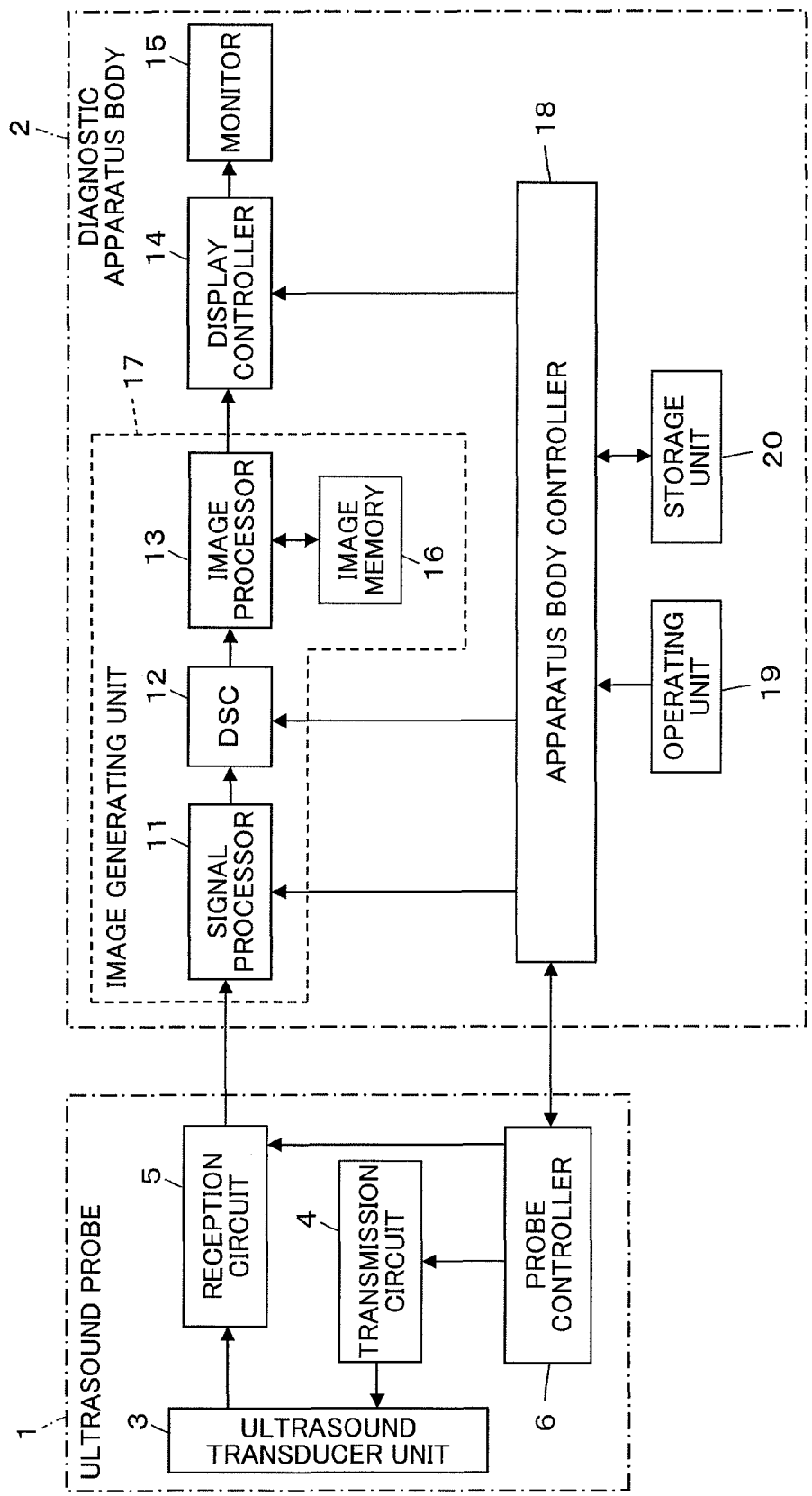
FIG. 1 is a block diagram illustrating a configuration of an ultrasound diagnostic apparatus according to an embodiment of the present invention.

FIG. 1 illustrates a configuration of an ultrasound diagnostic apparatus according to the embodiment. The ultrasound diagnostic apparatus comprises an ultrasound probe 1, and a diagnostic apparatus body 2 connected with the ultrasound probe 1.

The ultrasound probe 1 includes an ultrasound transducer unit 3, a transmission circuit 4 and a reception circuit 5 connected with the ultrasound transducer unit 3, as well as a probe controller 6 connected to the transmission circuit 4 and the reception circuit 5.

The diagnostic apparatus body 2 includes a signal processor 11 connected with the reception circuit 5 of the ultrasound probe 1, and with the signal processor 11, a digital scan converter (DSC) 12, an image processor 13, a display controller 14, and a monitor 15 are sequentially connected. The image processor 13 is also connected to an image memory 16, with the signal processor 11, the DSC 12, the image processor 13 and the image memory 16 constituting an image generating unit 17. An apparatus body controller 18 is connected to the signal processor 11, the DSC 12 and the display controller 14, while an operating unit 19 and a storage unit 20 are each connected to the apparatus body controller 18.

The probe controller 6 of the ultrasound probe 1 and the apparatus body controller 18 of the apparatus body 2 are connected with each other.

The ultrasound transducer unit 3 of the ultrasound probe 1 has a plurality of ultrasound transducers arrayed.

The transmission circuit 4 includes, for instance, a plurality of pulse generators, and is adapted to modify, based on the transmission delay pattern as selected in response to a control signal from the probe controller 6, the delay amounts of individual driving signals so that ultrasound waves transmitted from the ultrasound transducers of the ultrasound transducer unit 3 may form an ultrasonic beam, and then feed the driving signals to the ultrasound transducers, respectively.

The reception circuit 5 amplifies the reception signals as obtained by the individual ultrasound transducers of the ultrasound transducer unit 3 and subjects them to analog/digital conversion, then performs reception focusing on the signals. In the reception focusing process, the reception signals are provided with their respective delays in accordance with the sound speed or the sound speed distribution which is determined based on the reception delay pattern as selected in response to a control signal from the probe controller 6, then added together. The reception focusing allows sample data (sound ray signal) to be generated as data on a well-focused ultrasonic echo.

The probe controller 6 controls individual components of the ultrasound probe 1 based on various control signals transmitted from the apparatus body controller 18 of the diagnostic apparatus body 2.

The signal processor 11 of the diagnostic apparatus body 2 corrects the sample data as generated by the reception circuit 5 of the ultrasound probe 1 for attenuation due to distance in accordance with the depth of the position where ultrasound was reflected, then performs envelope demodulation on the data to generate the B-mode image signal which is tomographic image information on a tissue in the subject.

The DSC 12 subjects the B-mode image signal as generated by the signal processor 11 to the conversion (raster conversion) into an image signal compatible with the conventional television signal scanning method.

The image processor 13 performs various kinds of image processing, grayscaling and the like, as required on the B-mode image signal inputted from the DSC 12, and outputs the processed B-mode image signal to the display controller 14 or stores the signal in the image memory 16.

The display controller 14 controls the monitor 15 based on the B-mode image signal as subjected to image processing by the image processor 13 to display an ultrasound diagnostic image.

The monitor 15 includes a display device such as an LCD, and is adapted to display an ultrasound diagnostic image under the control of the display controller 14.

The operating unit 19 is used by an operator to perform input operations, and may be comprised of a keyboard, a mouse, a trackball, a touch panel, and the like.

The storage unit 20 is adapted to store operational programs and so forth, and a recording medium such as a hard disk, a flexible disk, MO, MT, RAM, CD-ROM, DVD-ROM, an SD card, a CF card and a USB memory, or a server is available for the unit 20.

The apparatus body controller 18 controls individual components of the diagnostic apparatus body 2 based on various instruction signals and the like inputted by an operator from the operating unit 19.

The signal processor 11, the DSC 12, the imaged processor 13, and the display controller 14 are implemented by a CPU associated with operational programs for giving the CPU instructions on various kinds of processing, while the above components may also be implemented by a digital circuitry.

Figure 2:
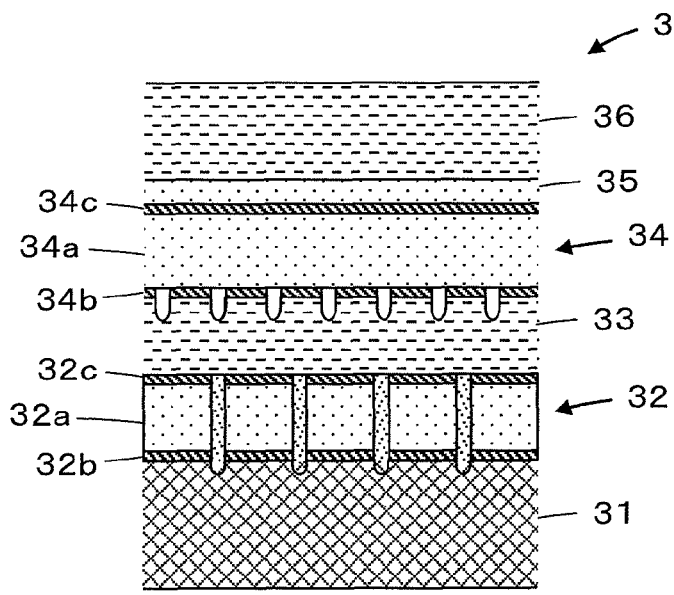
FIG. 2 is a cross-sectional view showing a structure of an ultrasound transducer unit as used in the embodiment.

FIG. 2 shows the structure of the ultrasound transducer unit 3.

A plurality of inorganic piezoelectric elements 32 are formed on the surface of a backing material 31 in an arrayed manner. The inorganic piezoelectric elements 32 have a plurality of inorganic piezoelectric bodies 32a separated from one another, with each inorganic piezoelectric body 32a having a signal line electrode layer 32b joined to one face thereof and a ground electrode layer 32c joined to another face. In other words, each inorganic piezoelectric element 32 has the inorganic piezoelectric body 32a of its own which is provided with the signal line electrode layer 32b and the ground electrode layer 32c.

On the inorganic piezoelectric elements 32 as such, an acoustic matching layer 33 is joined. The acoustic matching layer 33 is an integral layer extending over all the inorganic piezoelectric elements 32.

On the acoustic matching layer 33, a plurality of organic piezoelectric elements 34 are formed in an arrayed manner. The organic piezoelectric elements 34 have in common an organic piezoelectric body 34a extending over all the organic piezoelectric elements 34. On the surface of the organic piezoelectric body 34a that faces the acoustic matching layer 33, a plurality of signal line electrode layers 34b corresponding to the organic piezoelectric elements 34 are joined such that they are separated from one another, while a ground electrode layer 34c common to the organic piezoelectric elements 34, that is to say, extending over all the elements 34 is joined on the entire surface of the organic piezoelectric body 34a on the side opposite to the acoustic matching layer 33.

In other words, each organic piezoelectric element 34 is constructed of the signal line electrode layer 34b of its own as well as the organic piezoelectric body 34a and the ground electrode layer 34c both common to the organic piezoelectric elements 34. In consequence, the arraying pitch of the organic piezoelectric elements 34 solely depends on the arraying pitch of the signal line electrode layers 34b joined on the surface of the organic piezoelectric body 34a. In this embodiment, the signal line electrode layers 34b are arrayed at a pitch smaller than the arraying pitch of the inorganic piezoelectric elements 32, so that the organic piezoelectric elements 34 are formed in a manner that they are arrayed at a smaller pitch than the inorganic piezoelectric elements 32.

On the organic piezoelectric elements 34, an acoustic lens 36 is joined through a protective layer 35.

The inorganic piezoelectric bodies 32a of the inorganic piezoelectric elements 32 are formed of a piezoelectric ceramic typified by lead zirconate titanate (PZT) or a piezoelectric single crystal typified by lead magnesium niobate-lead titanate solid solution (PMN-PT). On the other hand, the organic piezoelectric body 34a of the organic piezoelectric elements 34 is formed of a polymeric piezoelectric material such as polyvinylidene fluoride (PVDF) or a polyvinylidene fluoride-trifluoroethylene copolymer.

The acoustic matching layer 33 has a thickness meeting $\lambda/4$ resonance conditions with respect to the wavelength $\lambda$ of a fundamental wave transmitted from the inorganic piezoelectric elements 32, and is formed of a material having an acoustic impedance of a medium value between the acoustic impedance values of the inorganic piezoelectric elements 32 and of the organic piezoelectric elements 34 so that it may allow ultrasound transmitted from the inorganic piezoelectric elements 32 to efficiently enter the inside of a subject.

Figure 3:
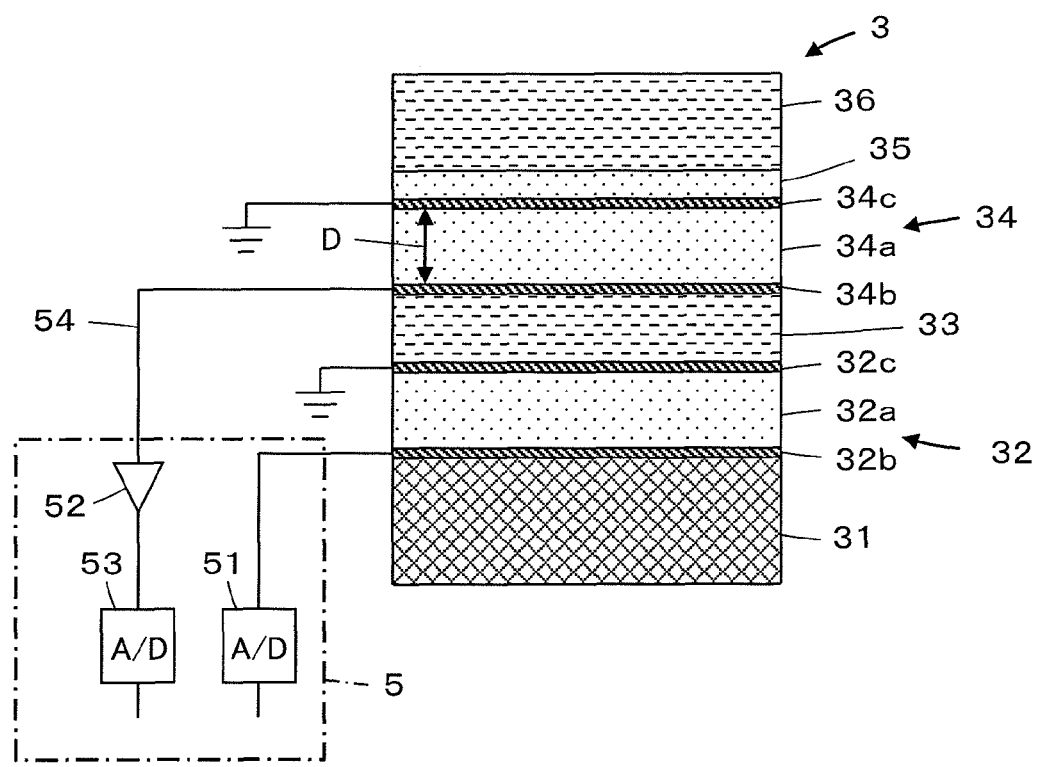
FIG. 3 is a diagram illustrating the connection between the ultrasound transducer unit and a reception circuit in the embodiment.

As seen from FIG. 3, the reception circuit 5 includes an analog/digital converter 51 connected to the signal line electrode layer 32b of each inorganic piezoelectric element 32, and an amplifier 52 and an analog/digital converter 53 connected to the signal line electrode layer 34b of each organic piezoelectric element 34 in this order through a transmission cable 54. The ground electrode layer 32c of each inorganic piezoelectric element 32 and the ground electrode layer 34c of each organic piezoelectric element 34 are both grounded.

Although not shown in FIG. 3, the transmission circuit 4 is connected to the signal line electrode layer 32b of each inorganic piezoelectric element 32.

The organic piezoelectric elements 34 as a whole are used as a second acoustic matching layer next to the acoustic matching layer 33 during the transmission of ultrasound by the inorganic piezoelectric elements 32. For this reason, the organic piezoelectric body 34a of each organic piezoelectric element 34 has a thickness D meeting $\lambda/4$ resonance conditions with respect to the wavelength $\lambda$ of a fundamental wave transmitted from the inorganic piezoelectric elements 32, and an acoustic impedance of a medium value between the acoustic impedance values of the acoustic matching layer 33 and of a subject as the living body.

As an example: The intrinsic acoustic impedance is about $35 \times 10^6$ (kg/m$^2$s) for lead zirconate titanate (PZT) constituting the inorganic piezoelectric bodies 32a, about $4 \times 10^6$ (kg/m$^2$s) for polyvinylidene fluoride (PVDF) constituting the organic piezoelectric body 34a, and about $1 \times 10^6$ to $2 \times 10^6$ (kg/m$^2$s) for biological substances except for bones. If the acoustic impedance of the acoustic matching layer 33 is set at a medium value between the acoustic impedance values of the inorganic piezoelectric bodies 32a and of the organic piezoelectric body 34a, the inorganic piezoelectric elements 32, the acoustic matching layer 33, the organic piezoelectric elements 34, and the subject will align in descending order of acoustic impedance, with an adequate matching effect being thus achieved.

During the reception of an ultrasonic echo, the organic piezoelectric elements 34 are used as non-resonant reception devices. In general, a polymeric piezoelectric material constituting the organic piezoelectric body 34a, such as polyvinylidene fluoride (PVDF) or a polyvinylidene fluoride-trifluoroethylene copolymer, is very low in mechanical quality factor Qm as compared with a piezoelectric ceramic such as lead zirconate titanate (PZT), and almost free of resonance during the reception of an ultrasonic echo in ultrasonography. Use of the organic piezoelectric elements 34 as non-resonant reception devices allows ultrasound in a wide wavelength range to be received, and reception signals to be made into images at a specified frequency.

The organic piezoelectric elements 34 as arrayed have such a very low capacitance of several to 10 pF, so that the transmission cable 54 connecting between the signal line electrode layer 34b of each organic piezoelectric element 34 and the corresponding amplifier 52 in the reception circuit 5 is limited in capacitance to being 0.1 to 5 times as high as the capacitance of the relevant organic piezoelectric element 34 in order to prevent attenuation of the reception signals as obtained by the organic piezoelectric elements 34. It is desirable, if possible, to connect the amplifier 52 with the signal line electrode layer 34b of the organic piezoelectric element 34 directly.

Operations of the apparatus of this embodiment are detailed below.

As an example, the inorganic piezoelectric elements 32 are used as transducers dedicated to ultrasound transmission, and the organic piezoelectric elements 34 are used as transducers dedicated to ultrasound reception.

In response to driving signals from the transmission circuit 4 of the ultrasound probe 1, a pulsed voltage or a continuous wave voltage is applied between the signal line electrode layer 32b and the ground electrode layer 32c of each inorganic piezoelectric element 32, and then the inorganic piezoelectric body 32a of each inorganic piezoelectric element 32 expands and contracts, leading to the generation of ultrasound in pulse or continuous wave form. The generated ultrasound waves enter the inside of a subject via the acoustic matching layer 33, the organic piezoelectric elements 34, the protective layer 35, and the acoustic lens 36. Since the organic piezoelectric elements 34 function as a second acoustic matching layer next to the acoustic matching layer 33, an adequate matching effect is achieved and the ultrasound waves enter into the subject efficiently.

The ultrasound waves having entered the inside of the subject are synthesized into an ultrasonic beam propagating in the subject.

If an ultrasonic echo from the subject enters the individual organic piezoelectric elements 34 via the acoustic lens 36 and the protective layer 35, the organic piezoelectric body 34a expands and contracts in response to a harmonic component of ultrasound with high sensitivity, so that an electric signal is generated between the signal line electrode layer 34b and the ground electrode layer 34c of each organic piezoelectric element 34, then outputted as a reception signal. Since the organic piezoelectric elements 34 are used as non-resonant reception devices, ultrasound in a wide wavelength range can be received, that is to say, even the nth harmonic of a fundamental wave transmitted form the inorganic piezoelectric elements 32, for instance, can be received.

The reception signal as outputted from the signal line electrode layer 34b of each organic piezoelectric element 34 is amplified by the corresponding amplifier 52 and subjected to analog/digital conversion by the corresponding analog/digital converter 53 in the reception circuit 5, and further subjected to reception focusing so as to generate sample data. In this regard, the reception signal is transmitted from the signal line electrode layer 34b of the relevant organic piezoelectric element 34 to the corresponding amplifier 52 in the reception circuit 5 via the transmission cable 54 which has a capacitance 0.1 to 5 times as high as that of the organic piezoelectric element 34, which allows the reception signal to be reduced in attenuation upon transmission.

Based on the sample data as generated by the reception circuit 5 according to the reception signals from the organic piezoelectric elements 34, an image signal for a harmonic image is generated by the image generating unit 17 of the diagnostic apparatus body 2, and the harmonic image is displayed on the monitor 15 by the display controller 14 based on the generated image signal.

It is thus possible to generate an ultrasound image by making the reception signals as obtained by the organic piezoelectric elements 34 into images at a specified frequency, the frequency of the nth harmonic of a fundamental wave transmitted from the inorganic piezoelectric elements 32, for instance.

The inorganic piezoelectric elements 32 may also be used as transducers adapted for both transmission and reception of ultrasound.

In that case, the ultrasonic echo as received by the organic piezoelectric elements 34 through the acoustic lens 36 and the protective layer 35 further enters the individual inorganic piezoelectric elements 32 through the organic piezoelectric elements 34 and the acoustic matching layer 33. The inorganic piezoelectric body 32a of each element 32 expands and contracts chiefly in response to the fundamental wave component of ultrasound, with an electric signal being generated between the signal line electrode layer 32b and the ground electrode layer 32c. The generated electric signal is outputted as a reception signal, and subjected to analog/digital conversion by the corresponding analog/digital converter 51 in the reception circuit 5.

Based on both the reception signals as obtained from the inorganic piezoelectric elements 32 and subjected to analog/digital conversion that correspond to the fundamental wave component and the reception signals as obtained from the organic piezoelectric elements 34 that correspond to the harmonic component, sample data is generated by the reception circuit 5, an image signal is generated by the image generating unit 17 of the diagnostic apparatus body 2, and an ultrasound image is displayed on the monitor 15 by the display controller 14 based on the generated image signal.

It is thus possible to generate the compound image in which the fundamental wave component and the harmonic component are compounded with each other.

In the embodiment as described above, the wavelength of ultrasound transmitted from the inorganic piezoelectric elements 32 can be specified at will because the organic piezoelectric elements 34 are used as non-resonant reception devices during the reception of an ultrasonic echo. In addition, a fundamental wave transmitted from the inorganic piezoelectric elements 32, as being of a broadband type, rarely involves so-called ringing, which allows an ultrasound image of high quality to be generated.

Since ultrasound in a wide wavelength range can be received by the organic piezoelectric elements 34, the depth resolution is improved, and the detection frequency/filter frequency can be set at any two or more values so as to improve the degree of freedom for image design.

The organic piezoelectric elements 34 are not necessarily formed at an arraying pitch smaller than the arraying pitch of the inorganic piezoelectric elements 32 but may be formed at an arraying pitch equal to or larger than that of the elements 32. If, however, the organic piezoelectric elements 34 are arrayed at a pitch smaller than the arraying pitch of the inorganic piezoelectric elements 32 as shown in FIG. 2, grating lobes will hardly occur even if a higher harmonic component is received by the organic piezoelectric elements 34, which also makes it possible to generate an ultrasound image of high quality.

The ultrasound probe 1 and the diagnostic apparatus body 2 may be connected with each other by wired connection or through wireless communication.

What is claimed is:

1. An ultrasound diagnostic apparatus comprising:
   inorganic piezoelectric elements arranged on a surface of a backing material in an arrayed manner at a first pitch;
   a first acoustic matching layer arranged on the inorganic piezoelectric elements extending over all the inorganic piezoelectric elements;
   organic piezoelectric elements arranged on the first acoustic matching layer in an arrayed manner at a second pitch smaller than the first pitch, each of the organic piezoelectric elements having a thickness meeting $\lambda/4$ resonance conditions with respect to a wavelength $\lambda$ of a fundamental wave transmitted from the inorganic piezoelectric elements
   a transmission circuit for transmitting ultrasound from the inorganic piezoelectric elements through the organic piezoelectric elements serving as a second acoustic matching layer;
   a reception circuit for using the organic piezoelectric elements as non-resonant reception devices to receive an ultrasonic echo and thereby obtain reception signals, transmitting the reception signals to amplifiers via transmission cables each having a capacitance 0.1 to 5 times as high as a capacitance of a corresponding organic piezoelectric element to amplify the reception signals, and performing reception focusing to generate sample data after analog/digital converting the reception signals; and
   an image generating unit for generating an ultrasound image based on the sample data generated by the reception circuit.

2. The ultrasound diagnostic apparatus according to claim 1, wherein the image generating unit generates an ultrasound image by making the reception signals as obtained by the organic piezoelectric elements into images at a specified frequency.

3. The ultrasound diagnostic apparatus according to claim 2, wherein the image generating unit generates an ultrasound image by making the reception signals as obtained by the organic piezoelectric elements into images at a frequency of an n-th harmonic of a fundamental wave transmitted from the inorganic piezoelectric elements.

4. The ultrasound diagnostic apparatus according to claim 1, wherein the reception circuit generates the sample data based both on reception signals obtained by the inorganic piezoelectric elements and on the reception signals obtained by the organic piezoelectric elements.

5. The ultrasound diagnostic apparatus according to claim 3, wherein the reception circuit generates the sample data based both on reception signals obtained by the inorganic piezoelectric elements and on the reception signals obtained by the organic piezoelectric elements.

6. The ultrasound diagnostic apparatus according to claim 1, wherein the organic piezoelectric elements have a capacitance of up to 10 pF.

7. The ultrasound diagnostic apparatus according to claim 1, wherein the organic piezoelectric elements are constructed of first signal line electrode layers corresponding to the organic piezoelectric elements, an organic piezoelectric body common to the organic piezoelectric elements, and a first ground electrode layer common to the organic piezoelectric elements.

8. The ultrasound diagnostic apparatus according to claim 7, wherein the first signal line electrode layers corresponding to the organic piezoelectric elements are separated from one another and joined on the surface of the organic piezoelectric body that faces the first acoustic matching layer.

9. The ultrasound diagnostic apparatus according to claim 8 wherein the inorganic piezoelectric elements are constructed of inorganic piezoelectric bodies, second signal line electrode layers and second ground electrode layers, each corresponding to the inorganic piezoelectric elements,
   the backing material, the second signal line electrode layers, the inorganic piezoelectric bodies, the second ground electrode layers, the first acoustic matching layer, the first signal line electrode layers, the organic piezoelectric body and the first ground electrode layer are stacked in the above order.

* * * * *